United States Patent
Oki

(10) Patent No.: US 7,662,354 B2
(45) Date of Patent: Feb. 16, 2010

(54) DEODORANT

(75) Inventor: Kazuo Oki, Wakayama (JP)

(73) Assignee: Kao Corporation, Tokyo (JP)

( * ) Notice: Subject to any disclaimer, the term of this patent is extended or adjusted under 35 U.S.C. 154(b) by 547 days.

(21) Appl. No.: 10/567,442

(22) PCT Filed: Aug. 6, 2004

(86) PCT No.: PCT/JP2004/011674

§ 371 (c)(1),
(2), (4) Date: Feb. 7, 2006

(87) PCT Pub. No.: WO2005/014059

PCT Pub. Date: Feb. 17, 2005

(65) Prior Publication Data

US 2008/0194447 A1    Aug. 14, 2008

(30) Foreign Application Priority Data

Aug. 8, 2003 (JP) .............................. 2003-290094

(51) Int. Cl.
*C01B 33/26* (2006.01)
*C01B 33/24* (2006.01)
*C01B 33/32* (2006.01)
*A61K 8/18* (2006.01)
*A61Q 15/00* (2006.01)
*A61K 8/58* (2006.01)
*C04B 35/00* (2006.01)

(52) U.S. Cl. .................. 423/328.2; 423/328.1; 423/331; 423/332; 424/65; 424/67; 424/68; 501/153; 501/154

(58) Field of Classification Search .............. 423/328.1, 423/328.2, 332, 327.1, 328.3, 331, 333, 334; 424/65, 67, 68; 501/153, 154
See application file for complete search history.

(56) References Cited

U.S. PATENT DOCUMENTS

| 4,959,268 | A | * | 9/1990 | Hagiwara et al. ............ 428/403 |
| 5,861,146 | A | * | 1/1999 | Peterson et al. ................ 424/65 |
| 5,883,035 | A | * | 3/1999 | Yang ............................ 502/81 |
| 5,885,599 | A | * | 3/1999 | Peterson et al. .............. 424/405 |
| 6,468,500 | B1 | * | 10/2002 | Sakaguchi et al. ........... 423/700 |
| 6,656,456 | B2 | * | 12/2003 | Dodd et al. .................... 424/67 |

FOREIGN PATENT DOCUMENTS

| EP | 0 282 287 A2 | 9/1988 |
| EP | 0 405 485 A2 | 1/1991 |
| JP | 2-277455 | 11/1990 |
| JP | 11-228127 | 8/1999 |
| JP | 2004-8518 | 1/2004 |
| WO | 00/38524 | 7/2000 |

OTHER PUBLICATIONS

U.S. Appl. No. 11/009,133, filed Dec. 13, 2004, Harima, et al.

* cited by examiner

*Primary Examiner*—Karl E Group
*Assistant Examiner*—Noah S Wiese
(74) *Attorney, Agent, or Firm*—Oblon, Spivak, McClelland, Maier & Neustadt, L.L.P.

(57) ABSTRACT

The present invention relates to use of an aluminosilicate particle for deodorization, wherein the aluminosilicate particle has the composition of: s $M(1)_xO_y$, t $M(2)_2O.Al_2O_3$ u $SiO_2$ v $R_mQ_n$, w $H_2O$, wherein M(1) is one or more members selected from the group consisting of Ag, Cu, Zn and Fe, M(2) is one or more members selected from the group consisting of Na, K and H, R is one or more members selected from the group consisting of Na, K, Ca and Mg, Q is one or more members selected from the group consisting of $CO_3$, $SO_4$, $NO_3$, and Cl, s satisfies $0<s\leq3$, and t satisfies $0\leq t\leq3$, with proviso that s+t is from 0.5 to 3, and u satisfies $0.5\leq u\leq6$, v satisfies $0<v\leq2$, w satisfies $w\geq0$, x satisfies $1\leq x\leq2$, y satisfies $1\leq y\leq3$, m satisfies $1\leq m\leq2$, and n satisfies $1\leq n\leq3$, and wherein the aluminosilicate particle has a specific surface area of 1 m²/g or more and less than 70 m²/g.

18 Claims, No Drawings

DEODORANT

FIELD OF THE INVENTION

The present invention relates to a deodorization in which a specified aluminosilicate particle is used.

BACKGROUND OF THE INVENTION

With the improvement of the living environment of recent years, there is an increasing desire of the removal of odor. Such odor includes, for example, an. alkaline odor from ammonia, amine or the like, an acidic odor from a lower fatty acid or the like, a sulfur-containing compound odor from a mercaptan or the like, and a neutral odor from an ester, a ketone, or an aldehyde or the like. It is important to remove a wide variety of these odors having different physical properties. As methods of removing foul odor, there have been known a masking method, an ozone oxidation method, a drug neutralization method, a microbial degradation method, an adsorption method and the like (see, for example, "*Atarashii Shoshu/dasshuzai to Gijutsu no Tenbo—Amenithi Shakai heno Apurouchi—(New Deodorant and Prospect for Technology—Approach to Amenity Society,*" authored by ICS Co., Ltd., TORAY RESEARCH CENTER, Inc., published in September, 1994, p. 12-24).

However, each of the above-mentioned methods has some disadvantages. For example, the masking method cannot be said as a method of essentially removing an odor; ozone is handled in the ozone oxidation method, thereby necessitating that facilities be large-scaled; in the drug neutralization method, a substance to be treated is limited to a neutralizable substance, thereby making an odor to be treated by the method limited; and the microbial degradation method does not give an immediate effect. Further, these methods have a disadvantage in safety when applied to a human body.

On the other hand, the adsorption method is a convenient method of deodorization having an immediate effect and being highly safe. An activated carbon is widely used as an adsorbent. However, the method has some disadvantages that the activated carbon has low deodorizing ability against ammonia, and that cleanliness might be lost when applied to a human body because of its black color. White deodorants include zeolite and activated clay, but the deodorants fall shorter in their deodorizing ability than the activated carbon.

In addition, among the household foul odors, a sulfur-containing foul odor itself from a mercaptan or hydrogen sulfide has a very low threshold value, so that it is recognized as a strong foul odor even when contained in a very small amount. Especially, a foul odor component generated from excretions, kitchen garbage and the like is mostly occupied by the sulfur-containing foul odor. Therefore, one having a strong deodorizing power has been desired for these foul odors.

SUMMARY OF THE INVENTION

The present invention provides:

[1] use of an aluminosilicate particle for deodorization, wherein the aluminosilicate particle has the composition of:

$$s\ M(1)_xO_y\ t\ M(2)_2O \cdot Al_2O_3\ u\ SiO_2\ v\ R_mQ_n\ w\ H_2O,$$

wherein M(1) is one or more members selected from the group consisting of Ag, Cu, Zn and Fe, M(2) is one or more members selected from the group consisting of Na, K and H, R is one or more members selected from the group consisting of Na, K, Ca and Mg, Q is one or more members selected from the group consisting of $CO_3$, $SO_4$, $NO_3$ and Cl, s satisfies $0 \leq s \leq 3$, and t satisfies $0 \leq t \leq 3$, with proviso that s+t is from 0.5 to 3, and u satisfies $0.5 \leq u \leq 6$, v satisfies $0 < v \leq 2$, w satisfies $w \geq 0$, x satisfies $1 \leq x \leq 2$, y satisfies $1 \leq y \leq 3$, m satisfies $1 \leq m \leq 2$, and n satisfies $1 \leq n \leq 3$, and wherein the aluminosilicate particle has a specific surface area of 1 $m^2/g$ or more and less than 70 $m^2/g$; and

[2] a method of using an aluminosilicate particle for deodorization, wherein the aluminosilicate particle has the composition of:

$$s\ M(1)_xO_y\ t\ M(2)_2O \cdot Al_2O_3\ u\ SiO_2\ v\ R_mQ_n\ w\ H_2O,$$

wherein M(1) is one or more members selected from the group consisting of Ag, Cu, Zn and Fe, M(2) is one or more members selected from the group consisting of Na, K and H, R is one or more members selected from the group consisting of Na, K, Ca and Mg, Q is one or more members selected from the group consisting of $CO_3$, $SO_4$, $NO_3$ and Cl, s satisfies $0 < s \leq 3$, and t satisfies $0 \leq t \leq 3$, with proviso that s+t is from 0.5 to 3, and u satisfies $0.5 \leq u \leq 6$, v satisfies $0 < v \leq 2$, w satisfies $w \geq 0$, x satisfies $1 \leq x \leq 2$, y satisfies $1 \leq y \leq 3$, m satisfies $1 \leq m \leq 2$, and n satisfies $1 \leq n \leq 3$, and wherein the aluminosilicate particle has a specific surface area of 1 $m^2/g$ or more and less than 70 $m^2/g$.

DETAILED DESCRIPTION OF THE INVENTION

The present invention has been accomplished in view of the prior arts as mentioned above, and relates to use of a pale colored, preferably white aluminosilicate particle for deodorization, wherein the aluminosilicate particle is capable of deodorizing odor derived from various causative substances generated in daily life environment, especially excellent in deodorizing ability against a sulfur-containing foul odor, and also safe to a human body, and furthermore exhibits excellent appearance upon application.

The aluminosilicate particle of the present invention is capable of exhibiting excellent deodorizing ability against various foul odors, for example, an alkaline odor derived from ammonia, amine, pyridine or the like, an acidic odor derived from a lower fatty acid or the like, and a neutral odor derived from an ester, a ketone, an aldehyde or the like. Among them, particularly excellent deodorizing ability can be exhibited against a sulfur-containing odor derived from methyl mercaptan, ethyl mercaptan, methyl sulfide, methyl disulfide, hydrogen sulfide or the like.

The embodiment upon use of the aluminosilicate particle of the present invention is not particularly limited, as long as the aluminosilicate particle is used for deodorization. The aluminosilicate particle may be described herein as a deodorant, from the viewpoint of its use as a deodorizing component.

One of the great features of the aluminosilicate particle of the present invention resides in that the aluminosilicate particle has specified composition and physical properties as described below. Since the aluminosilicate particle has the above constitution, the aluminosilicate particle is capable of exhibiting excellent deodorizing ability against foul odor derived from various causative substances. In particular, the aluminosilicate particle is capable of exhibiting excellent deodorizing ability against a sulfur-containing foul odor because the aluminosilicate particle contains a specified metal element. In addition, since the aluminosilicate particle has a pale color, preferably white color, the aluminosilicate particle is safe to a human body, and exhibits excellent appearance upon application.

The deodorant of the present invention contains an aluminosilicate particle specifically having the following composition:

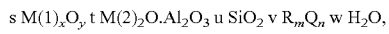

$$s\,M(1)_xO_y \cdot t\,M(2)_2O \cdot Al_2O_3 \cdot u\,SiO_2 \cdot v\,R_mQ_n \cdot w\,H_2O,$$

wherein M(1) is one or more members selected from the group consisting of Ag, Cu, Zn and Fe, M(2) is one or more members selected from the group consisting of Na, K and H, R is one or more members selected from the group consisting of Na, K, Ca and Mg, Q is one or more members selected from the group consisting of $CO_3$, $SO_4$, $NO_3$, and Cl, s satisfies $0<s\leq3$, and t satisfies $0\leq t\leq3$, with proviso that s+t is from 0.5 to 3, and u satisfies $0.5\leq u\leq6$, v satisfies $0<v\leq2$, w satisfies $w\geq0$, x satisfies $1\leq x\leq2$, y satisfies $1\leq y\leq3$, m satisfies $1\leq m\leq2$, and n satisfies $1\leq n\leq3$. Since the deodorant as referred to herein substantially contains the aluminosilicate particle itself, various physical properties of the particle which is the constituent, directly show the physical properties of the deodorant.

In the above-mentioned formula, M(1) is preferably Ag or Zn, from the viewpoint of increasing deodorizing power against the sulfur-containing foul odor and degree of whiteness of the powder. Here, when M(1) is composed of two or more kinds of elements, the item of s $M(1)_xO_y$ will be described for each item corresponding to each element. For example, when M(1) is composed of metal elements D and D', s $M(1)_xO_y$ can be described as $s_1\,D_{x1}O_{y1}\,s_2\,D'_{x2}O_{y2}$, with proviso that x1+x2=x, y1+y2=y, and $s_1+s_2=s$. The same can be said for the other items.

M(2) is preferably Na and/or H, from the viewpoint of exhibiting a high deodorizing ability and economic advantages. Also, R is preferably one or more members selected from the group consisting of Na, Ca and Mg, and more preferably Na, from the same viewpoint as in M(2). Q is preferably $CO_3$ and/or $NO_3$, from the viewpoint of facilitation of shape control of the particle.

s satisfies preferably $0<s\leq2$, and more preferably $0<s\leq1$, from the viewpoint of exhibiting a high deodorizing ability and economic advantages. t satisfies preferably $0\leq t\leq2$, and more preferably $0\leq t\leq1$, from the viewpoint of favorably keeping a pH of an aqueous dispersion of the deodorant of the present invention (1% by weight aqueous dispersion as described below). Here, s+t is preferably from 0.5 to 1.8, and more preferably from 0.6 to 1.5. u satisfies preferably $0.5\leq u\leq5$, and more preferably $0.5\leq u\leq4$, from the viewpoint of exhibiting a high deodorizing ability. v satisfies preferably $0<v\leq1.5$, and more preferably $0<v\leq1$, from the viewpoint of facilitation of shape control of the particle. w is a content of water (molar ratio) contained in the aluminosilicate particle, and varies depending upon the existing form of the aluminosilicate particle, for example, the powder, slurry form or the like. x and y, and m and n are respectively arbitrarily determined from a combination of M(1) and 0, and a combination of R and Q.

In addition, the aluminosilicate particle has a specific surface area of 1 m²/g or more and less than 70 m²/g, preferably from 1 to 65 m²/g, and more preferably from 30 to 65 m²/g, from the viewpoint of appropriately fixing or carrying a specified metal element as M(1) in the particle, and exhibiting an excellent deodorizing ability against the sulfur-containing foul odor. The specific surface area can be determined according to a method described later. The phrase "fixing or carrying" as used herein means a bond of a specified metal element as M(1) to the aluminosilicate particle by a physical and/or chemical binding strength.

The specific surface area of the aluminosilicate particle constituting the deodorant of the present invention can be adjusted to a given range by, for example, subjecting a raw material aluminosilicate particle (aluminosilicate particle to be used as the raw material) to an acid treatment as described later. The specific surface area or the like of the aluminosilicate particle is increased by the acid treatment, and the specific surface area can be adjusted to less than 70 m²/g by controlling the extent of acid treatment without performing excess acid treatment.

In addition, as the aluminosilicate particle constituting the deodorant of the present invention, a 1% by weight aqueous dispersion of the particle has a pH of preferably 7 or more, more preferably 8 or more, and even more preferably 9 or more, from the viewpoint of being excellent in deodorizing ability against the sulfur-containing foul odor. The pH of the 1% by weight aqueous dispersion of the aluminosilicate particle of the present invention can be determined by a method described later.

It is desired that the color of the aluminosilicate particle of the present invention satisfies an L* value of preferably 90 or more, and more preferably 95 or more, determined by "spectrophotometer SE2000," manufactured by Nippon Denshoku Kogyo from the viewpoint of its appearance and exhibition of high deodorizing ability.

In the aluminosilicate particle of the present invention, the M(1) component exhibits a deodorizing ability by adsorbing the sulfur-containing foul odor. Therefore, it is preferable that the M(1) component is present in a larger amount near the surface of the deodorant particle of the present invention, from the viewpoint of exhibiting an excellent deodorizing power. The concentration of the M(1) component at the surface can be expressed by a molar ratio of M(1) component atoms to Si atoms [M(1)/Si] and a molar ratio of M(1) component atoms to Al atoms [M(1)/Al] on the surface as determined by ESCA as shown in a method described later. The M(1)/Si is preferably 0.021 or more, and more preferably 0.040 or more. The M(1)/Al is preferably 0.025 or more, and more preferably 0.040 or more.

The aluminosilicate particle of the present invention has an average particle size of preferably from 0.1 to 1000 μm, more preferably from 0.4 to 600 μm, and even more preferably from 1 to 100 μm, from the viewpoint of securing favorable deodorization rate and favorable powder flowability. The average particle size is determined, for example, with a laser diffraction/scattering-type particle size distribution analyzer (LA-920, manufactured by HORIBA, Ltd.) at a relative refractive index of 1.16.

In addition, the shape of the aluminosilicate particle is not particularly limited. When applied to a human body, the shape is preferably in a spherical form, from the viewpoint of feel of use, such as spreadability and smoothness. Alternatively, the shape is preferably in an acicular, platy, columnar form or the like, from the viewpoint of improvement in yield upon addition to any carrier, for example, adhesion to paper, nonwoven fabric or the like. Among them, the aluminosilicate particle of the present invention preferably has a cancrinite-like form because the shape gives especially excellent adhesion to paper, nonwoven fabric or the like, and excellent exhibition of deodorizing ability. In addition, the cancrinite-like form is preferably in a sea urchin-like or tetrapod-like form, and more preferably a sea urchin-like shape.

The aluminosilicate particle may be amorphous or crystalline, and more preferably crystalline from the viewpoint of improving deodorizing ability against sulfur-containing foul odor. The aluminosilicate particle is obtained as an aggregate of acicular crystals, platy crystals, columnar crystals or the like, depending upon the preparation conditions. Alternatively, those crystals may be aggregated to form, for example, a spherical, tetrapod-like or massive aggregate, or a secondary aggregate thereof.

The term acicular form as referred to herein is one having a thickness of 500 nm or smaller, and a length as defined by its aspect ratio relative to the thickness of 2.0 or larger, the term platy form is one having a thickness of 300 nm or smaller, and a platy diameter as defined by its aspect ratio relative to the thickness of 2.0 or larger, and the term columnar form is one having a thickness of 50 nm or larger, and a length as defined by its aspect ratio relative to the thickness of 1.0 or larger and smaller than 2.0. In addition, the cancrinite-like form refers to those having one or more X-ray diffraction patterns selected from the group consisting of Nos. 20-379, 20-743, 25-776, 25-1499, 25-1500, 30-1170, 31-1272, 34-176, 35-479, 35-653, 38-513, 38-514, 38-515 and 45-1373 in a powder X-ray diffraction file published by JCPDS (Joint Committee on Powder Diffraction Standards). Also, in the X-ray diffraction patterns, those having a main peak at d=0.365±0.015 nm are preferable.

It is preferable that the aluminosilicate particle constituting the deodorant of the present invention is obtained, for example, by the steps of subjecting a raw material aluminosilicate particle having the composition in an anhydride form of:

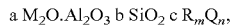
a $M_2O \cdot Al_2O_3$ b $SiO_2$ c $R_mQ_n$, wherein M is Na and/or K, R is one or more members selected from the group consisting of Na, K, Ca and Mg, Q is one or more members selected from the group consisting of $CO_3$, $SO_4$, $NO_3$ and Cl, a satisfies $0.5 \leq a \leq 3$, b satisfies $0.5 \leq b \leq 6$, c satisfies $0 < c \leq 2$, m satisfies $1 \leq m \leq 2$, and n satisfies $1 \leq n \leq 3$, to an acid treatment with an acid in an amount of 0 to 300 meq per 100 g of the raw material aluminosilicate particle (0 to 300 meq/100 g), and ion-exchanging with one or more metal ions selected from the group consisting of Ag, Cu, Zn and Fe.

In the above-mentioned formula, M is preferably Na. Here, when M is composed of Na and K, $aM_2O$ is expressed by $a_1Na_2O \cdot a_2K_2O$, with proviso that $a_1+a_2=a$. The same can be said for the other items. In addition, R is preferably one or more members selected from the group consisting of Na, Ca and Mg, and more preferably Na. Q is preferably $CO_3$ and/or $NO_3$. Further, a satisfies preferably $0.5 \leq a \leq 2.5$, and more preferably $0.5 \leq a \leq 2$. b satisfies preferably $0.5 \leq b \leq 5$, and more preferably $0.5 \leq b \leq 4$. c satisfies preferably $0 < c \leq 1.5$, and more preferably $0 < c \leq 1$. m and n are arbitrarily determined depending upon the combination of R and Q.

As the specific surface area of the raw material aluminosilicate particle, it is preferable that the specific surface area is of the same level as the aluminosilicate particle constituting the deodorant of the present invention. Also, it is preferable that its average particle size is of the same level as the aluminosilicate particle constituting the deodorant of the present invention. Further, the shape of the raw material aluminosilicate particle is not particularly limited, and it is preferable to have the above shapes in the same manner as the aluminosilicate particle constituting the deodorant of the present invention. Especially, when the raw material aluminosilicate particle is in a cancrinite-like form, it is preferable because the shape control of the aluminosilicate particle obtained therefrom as the deodorant is facilitated.

The process for preparing a raw material aluminosilicate particle used in the present invention is not particularly limited. The process for preparing a raw material aluminosilicate particle includes, for example, a process including the step of reacting an alumina raw material and a silica raw material in an aqueous alkali solution in the presence of $CO_3^{2-}$, $SO_4^{2-}$, $NO_3^-$, $Cl^-$ or the like.

The alumina raw material includes, for example, aluminum oxide, aluminum hydroxide, sodium aluminate and the like, and sodium aluminate is preferable. The silica raw material includes, for example, silica sand, quartz rock, water glass, sodium silicate, silica sol and the like, and water glass is preferable. Alternatively, as a raw material used as both of the alumina raw material and the silica raw material, there may be used, for example, a clay mineral such as kaolin, montmorillonite, bentonite, mica or talc, and an aluminosilicate mineral such as mullite.

The raw material of $CO_3^{2-}$ includes, for example, carbon dioxide gas, sodium carbonate, potassium carbonate, potassium sodium carbonate, calcium carbonate, magnesium carbonate and the like, and sodium carbonate is preferable.

The raw material of $SO_4^{2-}$ includes, for example, sulfuric acid, sodium sulfate, potassium sulfate, potassium sodium sulfate and the like, and sulfuric acid and sodium sulfate are preferable. The raw material of $NO_3^-$ includes, for example, nitric acid, sodium nitrate, potassium nitrate and the like, and nitric acid and sodium nitrate are preferable. The raw material of $Cl^-$ includes, for example, hydrochloric acid, sodium chloride, potassium chloride and the like, and hydrochloric acid and sodium chloride are preferable.

As an alkali for the aqueous alkali solution, there can be used, for example, an oxide such as sodium oxide or potassium oxide; a hydroxide such as sodium hydroxide or potassium hydroxide; a carbonate such as sodium carbonate, potassium carbonate or potassium sodium carbonate; a hydrogencarbonate such as sodium hydrogencarbonate or potassium hydrogencarbonate; or the like. There may be used as desired an oxide such as calcium oxide or magnesium oxide; a hydroxide such as calcium hydroxide or magnesium hydroxide; a carbonate such as calcium carbonate, magnesium carbonate or dolomite; a hydrogencarbonate such as calcium hydrogencarbonate or magnesium hydrogencarbonate; or the like.

The raw material aluminosilicate particle used in the present invention can be obtained by blending, mixing and reacting various compounds mentioned above in a given ratio. The blending ratio is appropriately determined depending on the composition of the resulting desired raw material aluminosilicate particle. Preferably, the molar ratio of blending components as a raw material of a raw material aluminosilicate particle is such that $M_2O/SiO_2$ is preferably from 0.01 to 100, and more preferably from 0.05 to 80, that $Al_2O_3/SiO_2$ is preferably from 0.01 to 10, and more preferably from 0.05 to 8, that $R_mQ_n/SiO_2$ is preferably from 0.01 to 100, and more preferably from 0.05 to 80, and that $H_2O/M_2O$ is preferably from 0.01 to 100, and more preferably from 0.05 to 80, when expressing the components as $M_2O$, $Al_2O_3$, $SiO_2$ and $R_mQ_n$ on the basis of. the constituting elements of each component.

Also, the reaction temperature during the preparation of the raw material aluminosilicate particle is preferably from 15° to 300° C., more preferably from 60° to 150° C., and even more preferably from 80° to 130° C., from the viewpoint of enhancing crystallinity of the raw material aluminosilicate particle and stabilizing its shape, and from the viewpoint of reducing chemical corrosion and. pressure load on a reaction vessel. The reaction time is preferably 2 hours or longer and 48 hours or shorter, from the viewpoint of completely carrying out the crystallization reaction.

As described above, the raw material aluminosilicate particle is usually obtained in the form of an aqueous dispersion (slurry). The solid content of the aqueous dispersion is preferably from 0.1 to 50% by weight.

Next, the raw material aluminosilicate particle obtained is subjected to an acid treatment with an acid in an amount of 0 to 300 meq per 100 g of the raw material aluminosilicate particle (0 to 300 meq/100 g). The acid treatment is carried out for the purpose of adjusting the pH of the slurry upon fixing or carrying the M(1) component to the raw material aluminosilicate by ion exchange. Upon fixing or carrying, it is preferable that the pH of the slurry is adjusted to pH of 7 or less, from the viewpoint exhibiting ion-exchange physical properties of the M(1) component. In addition, the acid treatment may be carried out for adjustment of specific surface area. The amount of the acid treatment is preferably from 6 to 300 meq/100 g, more preferably from 5 to 250 meq/100 g, and even more preferably from 20 to 140 meq/100 g, from the viewpoint of improving deodorizing ability and securing favorable color.

Here, the case of an acid treatment with an acid having 0 meq/100 g means a case where an acid treatment is not carried out. For example, when the raw material aluminosilicate particle has a specific surface area of 1 $m^2/g$ or more and less than 70 $m^2/g$, the raw material aluminosilicate may not be subjected to an acid treatment.

In the acid treatment of the raw material aluminosilicate particle, it is preferable to use a strong acid such as a hydrochloric acid, sulfuric acid or nitric acid, and especially preferably hydrochloric acid or nitric acid.

The acid treatment is specifically carried out by adding an aqueous solution containing the above-mentioned acid to the raw material aluminosilicate particle gradually or at one time, thereby contacting the particle with the acid. The acid may be added at a rate of preferably from 0.01 to 100 mL/min, and more preferably from 0.1 to 10 mL/min per 100 g of the raw material aluminosilicate particle.

In the acid treatment, the raw material aluminosilicate particle is made into a slurry state. The solid content of the reaction mixture is preferably from 1 to 50% by weight, from the viewpoint of securing flowability of the mixture (slurry), and preventing imbalance in the acid treatment, thereby improving the treatment efficiency.

The temperature during the acid treatment is preferably from 60° to 150° C., more preferably 80° to 120° C., from the viewpoint of increase in specific surface area and reduction in chemical or pressure load on the reaction vessel. Also, it is preferable that the acid treatment is carried out while properly stirring. The time period for the acid treatment after contacting the acid and the raw material aluminosilicate is preferably from 0.01 to 100 hours, and more preferably from 0.1 to 10 hours.

After the acid treatment, it is preferable that the reaction mixture is properly aged, for example, at 60° to 150° C. for about 0.1 to 10 hours.

Further, the aluminosilicate particle after the acid treatment is subjected to ion exchange with one or more metal ions selected from the group consisting of Ag, Cu, Zn and Fe. Alternatively, in the present invention, the raw material aluminosilicate particle having a desired specific surface area may be directly subjected to ion exchange without carrying out acid treatment. The ion exchange can be carried out, for example, by suspending the particle in water, and adding a compound containing the above-mentioned metal (hereinafter referred to as metal-containing compound) or an aqueous solution of the compound thereto, or immersing the particle in an aqueous solution of a metal-containing compound.

The raw material aluminosilicate particle is not necessarily subjected to ion exchange after the acid treatment as mentioned above. For example, as long as the metal-containing compound is allowed to coexist during the acid treatment, the acid treatment and ion exchange of the raw material aluminosilicate particle can be simultaneously carried out.

The above-mentioned metal-containing compound is not particularly limited, as long as the compound is a water-soluble metal-containing compound containing a desired metal. The compound includes, for example, a nitrate, a sulfate and a chloride, each containing a desired metal.

The ion exchange is usually carried out by suspending the raw material aluminosilicate particle in water while stirring. The solid content of the aqueous suspension of the raw material aluminosilicate particle is preferably from 1 to 50% by weight from the viewpoint of improving the efficiency of ion exchange.

The temperature at which the ion exchange is carried out is not particularly limited. The temperature is preferably from 20° to 120° C., and more preferably from 80° to 110° C. A required time period for the ion exchange is preferably from 0.01 to 2 hours, and more preferably from 0.02 to 1 hour, after contacting the raw material aluminosilicate particle and the metal-containing compound.

The amount ratio of the raw material aluminosilicate particle and the metal-containing compound during the ion exchange is such that the amount of the metal-containing compound is preferably from 0.1 to 30 parts by weight, more preferably from 0.2 to 10 parts by weight, and even more preferably from 0.5 to 5 parts by weight, based on 100 parts by weight of the raw material aluminosilicate particle.

In addition, after the ion exchange, it is preferable that the reaction mixture is properly aged, for example, at 60° to 150° C. for about 0.1 to about 10 hours.

It is most preferable that the metal component in the metal-containing compound is fixed to or carried in the aluminosilicate particle of the present invention by means of the ion exchange as described above. Alternatively, in place of the ion exchange, or in addition to the ion exchange, a metal component in the metal-containing compound may be fixed to or carried in the aluminosilicate particle by immersion method or precipitation method. During the preparation steps of the aluminosilicate particle constituting the deodorant of the present invention, the aluminosilicate particle may be properly washed for the purpose of removing impurities and the like at each point after the obtainment of the raw material aluminosilicate particle, after the acid treatment, and after the ion exchange. It is preferable that washing is carried out at a final stage of the preparation steps of the aluminosilicate particle, for example, after the obtainment of the raw material aluminosilicate and after the ion exchange.

Washing can be carried out by, for example, filtering an aqueous suspension of the aluminosilicate particle and washing the residue with water. The filter used in the filtration is not particularly limited, and, for example, a filter such as a Nutsche filter or filter press filter can be used.

After washing with water, the resulting aluminosilicate particle can be immediately used as the deodorant of the present invention. Alternatively, the aluminosilicate particle may be subjected to a desired treatment depending on the embodiment upon use of the deodorant. The embodiment upon use includes a filtration cake, a slurry, a dry powder and the like. The embodiment upon use may be selected in consideration of the application of the deodorant, and conditions in blending the aluminosilicate particle with other components to be added as desired for the deodorant. For example, when the aluminosilicate particle is prepared into a dry powder, the aluminosilicate particle obtained may be dried appropriately with a drier. The drier which can be used herein is not particularly limited, and includes, for example, a blast drier, a vacuum drier, a spray-drier and the like.

The deodorant of the present invention is capable of exhibiting excellent deodorizing ability against various foul odors including, for example, an alkaline odor derived from ammonia, amine, pyridine or the like, an acidic odor derived from a lower fatty acid or the like, and a neutral odor derived from an ester, a ketone, an aldehyde or the like. Among them, particularly excellent deodorizing ability can be exhibited against a sulfur-containing foul odor from methyl mercaptan, ethyl mercaptan, methyl sulfide, methyl disulfide, hydrogen sulfide or the like. In addition, the deodorant is capable of exhibiting highly excellent deodorizing ability on 3-mercapto-3-methylhexan-1-ol or the like which is a causative substance of under arm odor.

The deodorant of the present invention can be used in any given granular form or in any form of a molded article, such as a powdery, granular or pelletal form depending upon the desired use. When the deodorant is powdery, the deodorant does not have a roughened texture but has excellent feel of use when applied to a human body. On the other hand, when the deodorant has a granular or pelletal form, scattering of the deodorant can be suppressed, thereby having excellent handleability. In the molding of the deodorant into a granular form or molded article, there can be used an inorganic binder such as various clays or water glass, or an organic binder such as carboxymethyl cellulose, polyvinyl alcohol, various oils and various waxes. Furthermore, the deodorant of the present invention may be used as a mixture with an adsorbent or a photocatalyst, such as an activated clay, an activated carbon, silica gel, hydrotalcite, a clay mineral or titanium oxide. Therefore, as one embodiment of the present invention, the deodorant of the present invention may be used as a deodorizing composition containing the deodorant and other components mentioned above which are added depending upon use. The content of the deodorant of the present invention in the deodorizing composition is preferably from 0.1 to 50% by weight, more preferably from 0.5 to 50% by weight, and even more preferably from 1 to 50% by weight. This composition has an excellent deodorizing ability of the same level as that of the deodorant of the present invention.

One preferred example of the embodiment upon use of the deodorant of the present invention includes use for a body deodorant. The form of the body deodorant includes pump spray, stick, gel, soft solid, roll-on, powder spray, cream, lotion, powder, sheet and the like, and can be designed without any particular limitation. In these applications, the body deodorant can be prepared by properly blending the deodorant of the present invention together with known components which are used in the applications. The content of the deodorant of the present invention in each of those body deodorants is preferably from 0.01 to 50% by weight, more preferably from 0.1 to 30% by weight, and even more preferably from 0.3 to 10% by weight.

EXAMPLES

The following examples further describe and demonstrate embodiments of the present invention. The methods for determination of physical properties of the samples used in Examples and Comparative Examples are summarized hereinbelow.

(Methods for Determination of Physical Properties)

(1) Method for Determination of Specific Surface Area

The specific surface area was determined with FlowSorb Model 2300 (manufactured by Shimadzu Corporation). The sample used was 0.1 g, and a mixed gas of $N_2/He=30/70$ (volume ratio) was used as an adsorbing gas.

(2) Method for Determination of Deodorizing Ability i) Amount of Ammonia Deodorized Fifteen microliters of a 25% aqueous ammonia was added to a 1 L Tedlar bag (manufactured by Sansho Co., Ltd.), and 1 L of a nitrogen gas was poured into the bag, and the bag was tightly sealed. The bag was allowed to stand at room temperature for 3 hours, to vaporize an aqueous ammonia. This 1 L gas was used as an ammonia gas source for determination. Next, 0.1 g of a sample was placed into a 500 mL Erlenmeyer flask with ground joint, and 22 mL of a gas (concentration in the 500 mL Erlenmeyer flask: 80 ppm) was taken from the ammonia gas source for determination, and poured into the flask, and the flask was tightly sealed. After 10 minutes, a gas concentration was determined with a gas detecting tube (manufactured by Gastec Corporation, No. 3L), and the value obtained by subtracting the found value from 80 ppm was defined as an amount of ammonia deodorized (ppm/0.1 g particles).

ii) Amount of Methyl Mercaptan Deodorized

The amount 0.1 g of a sample was placed in a 500 mL Erlenmeyer flask with ground joint. Next, 40 µL of a methyl mercaptan standard solution (manufactured by Wako Pure Chemical Industries, Ltd.) (concentration in the 500 mL Erlenmeyer flask: 28 ppm) was poured into the flask, and the flask was tightly sealed. After 10 minutes, a gas concentration was determined with a gas detecting tube (manufactured by Gastec Corporation, No. 71). When the concentration of methyl mercaptan was 0 ppm at that point, 40 µL of the methyl mercaptan standard solution was additionally poured thereinto, to determine a gas concentration after 10 minutes. The procedures were repeated until a gas is detected, and a total absorption of methyl mercaptan being absorbed by the 0.1 g sample was defined as an amount of methyl mercaptan deodorized.

iii) Amount of Hydrogen Sulfide Deodorized

The amount 0.1 g of a sample was placed in a 500 mL Erlenmeyer flask with ground joint. Next, 8 mL of a 5000 ppm hydrogen sulfide gas (concentration in the 500 mL Erlenmeyer flask: 40 ppm) was poured into the flask, and the flask was tightly sealed. After 10 minutes, a gas concentration was determined with a gas detecting tube (manufactured by Gastec Corporation, No. 4LK). When the concentration of hydrogen sulfide was 0 ppm at that point, 8 mL of a 5000 ppm hydrogen sulfide gas was additionally poured thereinto, to determine a gas concentration after 10 minutes. The procedures were repeated until a gas is detected, and a total absorption of hydrogen sulfide being absorbed by the 0.1 g sample was defined as an amount of hydrogen sulfide deodorized.

(3) Method for Determination of pH of 1% by Weight Aqueous Dispersion

One gram of a sample was added to 99 g of ion-exchanged water (25° C.), and a pH of a slurry after stirring for 2 minutes was determined. The value obtained was defined as a pH of a 1% by weight aqueous dispersion.

(4) Method for Determination of Concentration of M(1) Component on Surface of Sample A sample was molded into the form of thin flakes with a pressing machine. Elemental determination of the surface of the sample [atoms of M(1) component, Si, Al] was carried out with ESCA-1000 manufactured by Shimadzu Corporation, to obtain a concentration ratio (molar ratio) of atoms on the surface from peak areas obtained of the elements.

(5) Method for Determination of Hue

A degree of whiteness L* of a sample was determined with "Spectrophotometer SE2000" manufactured by Nippon Denshoku Kogyo.

(6) Method for Determination of Average Particle Size

A particle size distribution of a dispersion prepared by dispersing a sample in an ion-exchanged water (relative refractive index: 1.16) as a dispersion medium with an ultrasonic wave for 1 minute was determined with a laser diffraction/scattering type particle size distribution analyzer (LA-920, manufactured by HORIBA, Ltd.). The median diameter obtained was defined as an average particle size.

Preparation Example 1

To a solution prepared by dissolving 94 g of sodium hydroxide in 1000 mL of ion-exchanged water, and further mixing therewith 130 g of nitric acid (61%) and 124 g of a sodium aluminate solution ($Na_2O$=19.8% by weight, $Al_2O_3$=25.9% by weight, $H_2O$=54.3% by weight) was added 127 g of water glass ($Na_2O$=9.8% by weight, $SiO_2$=29.6% by weight, $H_2O$=60.6% by weight) over 1 minute, and the components were reacted at 100° C. for 8 hours. After the reaction, the formed aluminosilicate particles were filtered and washed, and dried at 105° C. for 12 hours to give a powder of raw material aluminosilicate particles. The resulting raw material aluminosilicate particles had a porous spherical shape in which acicular crystals are aggregated. The resulting raw material aluminosilicate particles were subjected to X-ray diffraction using a powder X-ray diffractometer [RINT2500, manufactured by Rigaku Corporation]. As a result, the aluminosilicate particles had diffraction patterns corresponding to powder X-ray diffraction file No. 38-513 published by JCPDS.

Preparation Example 2

To a solution prepared by dissolving 103 g of sodium hydroxide in 1000 mL of ion-exchanged water, and further mixing therewith 157 g of a sodium aluminate solution ($Na_2O$=19.8% by weight, $Al2O3$=25.9% by weight, $H_2O$=54.3% by weight) was added 259 g of water glass ($Na_2O$=9.8% by weight, $SiO_2$=29.6% by weight, $H_2O$=60.6% by weight) over 1 minute, and the components were reacted at 100° C. for 2 hours. Thereafter, a solution obtained by mixing a solution prepared by dissolving 32 g of sodium hydroxide in 110 mL of ion-exchanged water, with 124 g of nitric acid (61%) was additionally added thereto over 1 minute, and the components were further reacted at 100° C. for 10 hours. After the reaction, the formed aluminosilicate particles were filtered and washed, and dried at 105° C. for 12 hours to give a powder of raw material aluminosilicate particles. The resulting raw material aluminosilicate particles were aggregates of columnar and acicular crystals to have a grown form into a tetrapod-like shape. The resulting raw material aluminosilicate particles were subjected to X-ray diffraction using a powder X-ray diffractometer [RINT2500, manufactured by Rigaku Corporation]. As a result, the aluminosilicate particles had diffraction patterns corresponding to JCPDS No. 38-513.

The compositions and the physical properties of the raw material aluminosilicates obtained in Preparation Examples 1 and 2 are summarized in Table 1.

TABLE 1

| | Composition | Particle Shape | Specific Surface Area ($m^2/g$) |
|---|---|---|---|
| Prep. Ex. 1 | $Na_2O \cdot Al_2O_3 2SiO_2 0.4NaNO_3 0.7H_2O$ | Sea Urchin-Like Cancrinite | 40 |
| Prep. Ex. 2 | $Na_2O \cdot Al_2O_3 2.5SiO_2 0.5NaNO_3 0.4H_2O$ | Tetrapod-Like Cancrinite | 4.6 |

Examples 1 to 6 and Comparative Examples 1 and 2

Each of the deodorants of Examples 1 to 6 and Comparative Examples 1 and 2 was prepared in accordance with the listing of "Preparation Example of Deodorant" of the following Table 2.

TABLE 2

| | Preparation Examples of Deodorants | | | |
|---|---|---|---|---|
| | Raw Material Aluminosilicate Particles | Dropping Amount of 61% Nitric Acid (mL/100 g Particles) | Amount of Acid Treated (meq/100 g Particles) | Amount of Silver Nitrate (g/100 g particles) |
| Ex. 1 | Prep. Ex. 1 | 0 | 0 | 3.94 |
| Ex. 2 | Prep. Ex. 1 | 2 | 26 | 3.94 |
| Ex. 3 | Prep. Ex. 1 | 10 | 131 | 3.94 |
| Comp. Ex. 1 | Prep. Ex. 1 | 20 | 263 | 3.94 |
| Ex. 4 | Prep. Ex. 2 | 0 | 0 | 3.94 |
| Ex. 5 | Prep. Ex. 2 | 2 | 26 | 3.94 |
| Ex. 6 | Prep. Ex. 2 | 10 | 131 | 3.94 |
| Comp. Ex. 2 | Prep. Ex. 2 | 80 | 1051 | 3.94 |

One-hundred grams of the raw material aluminosilicate particles obtained in Preparation Example 1 or 2 were suspended in 900 mL of ion-exchanged water, and the mixture was kept at 100° C. While stirring, a given amount of 61% nitric acid was added dropwise at a rate of 1 mL/minute to properly carry out an acid treatment. Next, an aqueous silver nitrate prepared by dissolving 3.94 g of silver nitrate in 30 g of ion-exchanged water was supplied thereto, and the mixture was kept at 100° C. for 1 hour to carry out ion exchange. Thereafter, the resulting product was filtered, washed with water, and dried at 105° C. for 12 hours, to give a white aluminosilicate-based deodorant.

The compositions and the physical properties of the aluminosilicate particles constituting the deodorants of Examples 1 to 6 and Comparative Examples 1 and 2, and the deodorizing abilities of the deodorants are summarized in Table 3. In addition, the average particle sizes of the aluminosilicate particles are summarized in Table 4.

TABLE 3

| Composition | Particle Shape | Specific Surface Area ($m^2/g$) | Deodorizing Ability (ppm/0.1 g particles) | | | pH of 1% by Weight Aqueous Dispersion | Hue | Ag Conc. on Surface | |
|---|---|---|---|---|---|---|---|---|---|
| | | | Ammonia | Methyl Mercaptan | Hydrogen Sulfide | | | Ag/Si | Ag/Al |
| E. 1  $0.05Ag_2O \cdot 0.9Na_2O \cdot Al_2O_3 2SiO_2 0.4NaNO_3 0.7H_2O$ | U | 44.7 | 72.3 | 489 | 267 | 10.04 | 93.8 | 0.075 | 0.070 |
| E. 2  $0.05Ag_2O \cdot 0.8Na_2O \cdot Al_2O_3 2SiO_2 0.4NaNO_3 0.8H_2O$ | U | 45.8 | 78 | 495 | 275 | 9.78 | 95.8 | 0.049 | 0.056 |
| E. 3  $0.05Ag_2O \cdot 0.6Na_2O \cdot Al_2O_3 2SiO_2 0.4NaNO_3 0.9H_2O$ | U | 63.1 | 58 | 469 | 236 | 9.22 | 96.6 | 0.025 | 0.030 |
| C. 1  $0.05Ag_2O \cdot 0.3Na_2O \cdot Al_2O_3 2SiO_2 0.3NaNO_3 1.8H_2O$ | U | 88.8 | 79 | 345 | 189 | 8.41 | 96.3 | 0.020 | 0.024 |
| E. 4  $0.05Ag_2O \cdot 0.8Na_2O \cdot Al_2O_3 2.5SiO_2 0.5NaNO_3 0.8H_2O$ | T | 4.4 | 43 | 153 | 75 | 9.29 | 94.4 | 0.093 | 0.141 |
| E. 5  $0.05Ag_2O \cdot 0.8Na_2O \cdot Al_2O_3 2.5SiO_2 0.5NaNO_3 0.8H_2O$ | T | 7.3 | 40 | 213 | 112 | 9.21 | 96.7 | 0.068 | 0.041 |
| E. 6  $0.05Ag_2O \cdot 0.6Na_2O \cdot Al_2O_3 2.5SiO_2 0.4NaNO_3 1.3H_2O$ | T | 27.5 | 67 | 133 | 69 | 8.46 | 96.9 | 0.022 | 0.029 |
| C. 2  $0.05Ag_2O \cdot Al_2O_3 2.5SiO_2 0.2NaNO_3 4.4H_2O$ | T | 100 | 80 | 16 | 4 | 5.45 | 96.4 | 0.009 | 0.016 |

In the table, "E" stands for Example, and "C" stands for Comparative Example. Also, "U" stands for sea urchin-like cancrinite, and "T" stands for tetrapod-like cancrinite.

TABLE 4

| | Average Particle Size (μm) |
|---|---|
| Ex. 1 | 8.3 |
| Ex. 2 | 6.8 |
| Ex. 3 | 9.8 |
| Comp. Ex. 1 | 10.7 |
| Ex. 4 | 8.3 |
| Ex. 5 | 6.8 |
| Ex. 6 | 9.8 |
| Comp. Ex. 2 | 4.7 |

It can be seen from Table 3 that the deodorants of Examples 1 to 6 exhibit the same level of deodorizing abilities against ammonia, an alkaline odor, while exhibiting especially excellent deodorizing abilities against methyl mercaptan and hydrogen sulfide, sulfur-containing foul odors, as compared to those deodorants of Comparative Examples 1 and 2. In addition, it can be seen that the deodorizing ability against the sulfur-containing foul odors are more excellent in the aluminosilicate particles having a particle shape in the form of a sea urchin-like cancrinite than those in the form of a tetrapod-like cancrinite.

Test Example 1 Evaluation of Use as Body Deodorant

To 4 test individuals having an apocrine odor was applied 0.5 g of the following deodorant-containing product (inventive product) as a test sample to one under arm, and 0.5 g of a control (comparative product) to the other under arm, and the test individuals were asked to wear T-shirts with cotton pads.

Each of the cotton pads was collected after 8 hours, and the level of odor was judged by three specialists for the evaluation. The level of odor was evaluated in 11 ranks including a midpoint of each level in accordance with the following evaluation criteria. An average for each test individual was obtained, and an average of the odor level four test individuals was further obtained and defined as the odor level for each test product.

(Evaluation Criteria for Odor)
5: Very strongly odorous;
4: Strongly odorous;
3: Slightly strongly odorous;
2: Recognizably odorous;
1: Slightly odorous;
0: Odorless.

(1) Pump-Spray Composition (Example 7, Comparative Example 3)

| (Raw Material) | Inventive Product (% by weight) | Comparative Product (% by weight) |
|---|---|---|
| Aluminosilicate-Based Deodorant (Example 2) | 0.5 | 0 |
| Aluminum Chlorohydrate (Locron P, manufactured by Hoechst Japan, Limited) | 3 | 3 |
| Octamethyl Cyclotetrasiloxane (Silicone SH-244, manufactured by Toray Dow Corning Silicone) | 96.5 | 97 |
| Total | 100 | 100 |

The odor level of the above deodorant-containing product (inventive product) and the control (comparative product) was obtained as follows.

Deodorant-Containing Product (Inventive Product): 1.88

Control (Comparative Product): 2.63

(2) Stick Composition (Example 8, Comparative Example 4)

| (Raw Material) | Inventive Product (% by weight) | Comparative Product (% by weight) |
|---|---|---|
| Aluminosilicate-Based Deodorant (Example 2) | 1 | 0 |
| Stearyl Alcohol | 16 | 16 |
| Behenyl Alcohol | 0.6 | 0.6 |
| Hardened Castor Oil | 3.25 | 3.25 |
| PPG-14 Butyl Ether | 3 | 3 |
| C12-15 Alkyl Benzoate | 4 | 4 |
| Decamethyl Cyclopentasiloxane (SH-245, manufactured by Toray Dow Corning Silicone) | 41.15 | 42.15 |
| Aluminum Zirconium Tetrachlorohydrex Glycine Complex (REACH AZP-908SUF, manufactured by REHEIS) | 24 | 24 |
| Talc | 7 | 7 |
| Total | 100 | 100 |

The odor level of the above deodorant-containing product (inventive product) and the control (comparative product) was obtained as follows.

Deodorant-Containing Product (Inventive Product): 2.38
Control (Comparative Product): 3.13

It can be seen from the evaluation results of the above-mentioned (1) to (2) that excellent deodorizing ability can be obtained in any of the forms of the inventive products. In addition, the evaluations were made in the same manner for the following (3) to (6). As a result, an excellent deodorizing ability was obtained.

(3) Powder Spray Composition (Example 9)

Each of the components except for LPG was uniformly mixed and filled in an aerosol vessel, and clinched. Thereafter, LPG was introduced under pressure, to give a powder spray manufactured article.

| (Raw Material) | (% by weight) |
| --- | --- |
| Aluminosilicate-Based Deodorant (Example 1) | 1 |
| Aluminum Chlorohydrate (Locron P, manufactured by Hoechst Japan Limited) | 3 |
| Talc | 2.5 |
| Isopropyl Methyl Phenol | 0.02 |
| Isopropyl Myristate | 2.5 |
| Dimethyl Silicone (10 cs) | 0.06 |
| BHT | 0.02 |
| Perfume | 0.2 |
| Decamethyl Cyclopentasiloxane (SH-245, manufactured by Toray Dow Corning Silicone) | 0.7 |
| LPG | 90 |

(4) Roll-on Composition (Example 10)

Each of the components shown below was uniformly mixed and filled in a roll-on vessel.

| (Raw Material) | (% by weight) |
| --- | --- |
| Aluminosilicate-Based Deodorant (Example 3) | 0.5 |
| Silicone Resin (KMP-590, manufactured by Shin-Etsu Chemical Co., Ltd.) | 1 |
| Aluminum Chlorohydrate (REACH 501 solution, manufactured by REHEIS) | 15 |
| Neopentyl Glycol Dicaprate (ESTEMOL N-01, manufactured by THE NISSIN OIL MILLS, LTD.) | 0.1 |
| Polyethylene Glycol (Molecular Weight: 400) | 1 |
| Perfume | 0.3 |
| 95% Ethanol | 80 |
| Purified Water | 2.1 |

(5) Pump-Spray Composition (Example 11)

Each of the components shown below was uniformly mixed and filled in a pump vessel.

| (Raw Material) | (% by weight) |
| --- | --- |
| Aluminosilicate-Based Deodorant (Example 2) | 0.3 |
| Aluminum Chlorohydrate (REACH 501 solution, manufactured by REHEIS) | 5 |
| Tricosane | 0.2 |
| Polyoxyethylene(20 EO) Palm Oil Fatty Acid Sorbitan (RHEODOL TW-L120, Manufactured by Kao Corporation) | 0.3 |
| Butylene Glycol | 5 |
| Perfume | 0.2 |
| Purified Water | 2 |
| Ethanol | 87 |

(6) Pump Spray Composition (Example 12)

Each of the components shown below was uniformly mixed and filled in a pump vessel.

| (Raw Material) | (% by weight) |
| --- | --- |
| Aluminosilicate-Based Deodorant (Example 1) | 3 |
| Tricosane | 0.2 |
| Perfume | 0.2 |
| Isopropyl Palmitate | 5 |
| Octamethyl Cyclotetrasiloxane (Silicone SH-244, manufactured by Toray Dow Corning Silicone) | 91.6 |

Test Example 2 Evaluation for Deodorizing Ability Against Model Armpit Odor

As a pseudo-under arm odor perspiration, a physiological saline of 3-mercapto-3-methylhexan-1-ol (S-form: R-form=72:28, weight ratio) was prepared (concentration: 10, 50 or 100 ppm (weight ratio)).

A mixture of 10 mg of the deodorant obtained in Example 2, or 6 g of talc, an activated carbon 1, an activated carbon 2, activated clay, zinc oxide, or silver-based zeolite, and 6 g of the physiological saline of 3-mercapto-3-methylhexan-1-ol was placed in a glass test tube in an amount of 6 g each, and the glass test tube was tightly sealed. The test tube was stirred with a mixer for 2 minutes, and centrifuged (3000 rpm for 10 minutes). The supernatant was filtered with a filter (cellulose acetate, 0.45 μm, manufactured by Toyo Roshi Kaisha, Ltd.). Five grams of the filtrate and 2.5 g of sodium chloride were placed in a separate test tube, and the mixture was stirred for 1 minute. One gram of hexane was added thereto, and stirred for 2 minutes, and the mixture was allowed to stand for 3 minutes. The amount 0.5 g of the supernatant was taken out with a pipette, and placed in a vial for GC-MS determination. According to GC-MS analysis, an area of the peak ascribed to m/z=97, a mass fragment characteristic to 3-mercapto-3-methylhexan-1-ol was determined.

As a blank test, a peak area when the same procedures were carried out without adding a deodorant was determined. From these determinations, a deodorized percentage of 3-mercapto-3-methylhexan-1-ol was obtained in accordance with the following formula:

Deodorized Percentage (%)=[1−(Peak Area When Adding Deodorant/Peak Area When Not Adding Deodorant)]×100

Here, the conditions for GC-MS analysis are as follows.

Apparatus: 6890GC-5973MSD (manufactured by Agilent Technologies)

Column: DB-1 (60 m×0.25 mm×0.25 μm)
Programming Setting: 40° C. (1 minute)→(6° C./minute)→60° C.→(2° C./minute)→300° C. (40 minutes)
Carrier Gas: He
Ionization Potential: 70 eV The results are shown in Table 5.

TABLE 5

| Deodorized Percentage (%) | 3-Mercapto-3-methylhexane-1-hexan-1-ol | | |
|---|---|---|---|
| | 10 ppm | 50 ppm | 100 ppm |
| Blank | 0 | 0 | 0 |
| Deodorant of Ex. 2 | 100 | 100 | 72 |
| Talc | 23 | 10 | 5 |
| Activated Carbon 1 | 100 | 100 | 98 |
| Activated Carbon 2 | 81 | 74 | 61 |
| Activated Clay | 14 | 12 | 9 |
| Zinc Oxide | 23 | 12 | 12 |
| Silver-Based Zeolite | 65 | 14 | 8 |

It can be seen from Table 5 that the deodorant (aluminosilicate particles) of the present invention is capable of exhibiting a highly excellent deodorizing ability against 3-mercapto-3-methylhexan-1-ol, which is an under arm odor causative substance. Although a deodorizing ability of the same level or higher is exhibited in the activated carbon 1 as in the deodorant of the present invention, cleanliness might be lost when the activated carbon is applied to a human body because of its black color. On the other hand, the deodorant of the present invention is free from the concern as in the case of an activated carbon because of its pale to white color, so that the deodorant can be applied to a human body without any limitations. Therefore, it can be said to be a deodorization component which is more excellent for use in body deodorants.

According to the present invention, a pale colored, preferably white aluminosilicate particle for deodorization, wherein the aluminosilicate particle is capable of deodorizing odor derived from various causative substances generated in daily life environment, especially sulfur-containing foul odor, and also safe to a human body, and furthermore exhibits excellent appearance upon application is provided.

The invention claimed is:

1. A method comprising deodorizing in the presence of a deodorant comprising crystalline aluminosilicate particles, wherein the aluminosilicate particles have a composition of:

$$s\,M(1)_xO_y.t\,M(2)_2O.Al_2O_3.u\,SiO_2.v\,R_mQ_{n.w}\,H_2O,$$

wherein M(1) is one or more members selected from the group consisting of Ag, Cu, Zn and Fe, M(2) is one or more members selected from the group consisting of Na, K and H, R is one or more members selected from the group consisting of Na, K, Ca and Mg, Q is one or more members selected from the group consisting of $CO_3$, $SO_4$, $NO_3$, and Cl, s satisfies $0<s\leq3$, and t satisfies $0\leq t\leq3$, with proviso that s+t is from 0.5 to 3, and u satisfies $0.5\leq u\leq6$, v satisfies $0<v\leq2$, w satisfies $w\geq0$, x satisfies $1\leq x\leq2$, y satisfies $1\leq y\leq3$, m satisfies $1\leq m\leq2$, and n satisfies $1\leq n\leq3$, wherein the aluminosilicate particle has a specific surface area of 1 m$^2$/g or more and less than 70 m$^2$/g, and wherein the aluminosilicate particle is obtained by subjecting a raw material aluminosilicate particle having the composition in an anhydride form of:

$$a\,M_2O.Al_2O_3.b\,SiO_2.c\,R_mQ_n,$$

wherein M is Na and/or K, R is one or more members selected from the group consisting of Na, K, Ca and Mg, Q is one or more members selected from the group consisting of $CO_3$, $SO_4$, $NO_3$, and Cl, a satisfies $0.5\leq a\leq3$, b satisfies $0.5\leq b\leq6$, c satisfies $0<c\leq2$, m satisfies $1\leq m\leq2$, and n satisfies $1\leq n\leq3$, to an acid treatment with a strong acid in an amount of 5 to 250 meq per 100 g of the raw material aluminosilicate particle (5 to 250 meq/100 g), and ion-exchanging with one or more metal ions selected from the group consisting of Ag, Cu, Zn and Fe.

2. The method according to claim 1, wherein a 1% by weight aqueous dispersion of the aluminosilicate particle has a pH of 7 or more.

3. The method according to claim 1, wherein a sulfur-containing odor is deodorized.

4. The method according to claim 1, wherein M(1) is Ag or Zn, M(2) is at least one of Na and H, Q is at least one of $CO_3$ and $NO_3$, $0<s\leq2$, $0\leq t\leq1$, s +t is from 0.6 to 1.5, $0.5\leq u\leq4$, $0<v\leq1$.

5. The method according to claim 1, wherein the aluminosilicate particle has a specific surface area of from 30 to 65 m$^2$/g.

6. The method according to claim 2, wherein said pH is 9 or more.

7. The method according to claim 1, wherein the aluminosilicate particle has a color that satisfies an L* value of 95 or more.

8. The method according to claim 1, wherein the aluminosilicate particle has an average particle size of from 0.4 to 600 μm.

9. The method according to claim 1, wherein the aluminosilicate particle has a shape selected from the group consisting of spherical, acicular, platy, columnar and cancrinite.

10. The method according to claim 9, wherein the shape is cancrinite, having a sea urchin shape.

11. The method according to claim 1, wherein said acid treatment is with an acid in an amount of 20 to 140 meq/100 g.

12. The method according to claim 1, wherein the deodorant is in the form of a powder, granules, or pellets.

13. The method according to claim 1, wherein the deodorant is in the form of a composition additionally comprising at least one of an inorganic binder, organic binder, adsorbent, and a photocatalyst.

14. The method according to claim 1, wherein the deodorant is present in a composition and having a content of from 1 to 50% by weight in the composition.

15. The method according to claim 1, wherein the deodorizing is of a human body.

16. The method according to claim 15, wherein the deodorant is present in a composition and having a content of 0.3 to 10% by weight of the composition.

17. The method according to claim 1, wherein the aluminosilicate particle has a cancrinite-like form having an X-ray diffraction pattern selected from the group consisting of Nos. 20-379, 20-743, 25-776, 25-1499, 25-1500, 30-1170, 31-1272, 34-176, 35-479, 35-653, 38-513, 38-514, 38-515 and 45-1373, in a powder X-ray diffraction file published by Joint Committee on Powder Diffraction Standards (JCPDS).

18. The method according to claim 1, wherein the strong acid is hydrochloric acid, sulfuric acid or nitric acid.

* * * * *

UNITED STATES PATENT AND TRADEMARK OFFICE
CERTIFICATE OF CORRECTION

PATENT NO. : 7,662,354 B2
APPLICATION NO. : 10/567442
DATED : February 16, 2010
INVENTOR(S) : Kazuo Oki It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 757 days.

Signed and Sealed this

Thirtieth Day of November, 2010

David J. Kappos
*Director of the United States Patent and Trademark Office*